United States Patent [19]

Curtis

[11] 4,098,885
[45] Jul. 4, 1978

[54] EQUINE ANTHELMINTIC

[75] Inventor: Ralston Curtis, Los Altos, Calif.

[73] Assignee: Zoecon Corporation, Palo Alto, Calif.

[21] Appl. No.: 842,126

[22] Filed: Oct. 14, 1977

[51] Int. Cl.$^2$ ............................................. A61K 31/66
[52] U.S. Cl. .................................................... 424/212
[58] Field of Search .......................................... 424/212

[56] References Cited
U.S. PATENT DOCUMENTS 3,584,126  6/1971  Greenberg ........................... 424/212

Primary Examiner—Sam Rosen
Attorney, Agent, or Firm—Donald W. Erickson

[57] ABSTRACT

A novel composition comprising the equine anthelmintic, butonate, in a gel formulation and preparation thereof.

9 Claims, No Drawings

EQUINE ANTHELMINTIC

This invention relates to a novel composition for the control of endoparasites in equine and the preparation thereof. More particularly, this invention relates to a novel gel composition containing butonate for the control of equine endoparasites.

Endoparasites invariably gain access to the inner organs of equine by way of the animal's mouth. Generally, the endoparasite is found in the animal's mouth during the egg and first larval stage of the insect's life cycle. The larvae adhere and/or burrow into the tongue, cheeks, and inner lips of the animal until developed to the second larval stage, whereupon the endoparasites migrate to the stomach and intestines where they reside in the walls thereof until the pupal stage is reached. The pupae are passed out of the body and then develop into adult insects to complete the cycle. Depending upon the degree of infestation, endoparasites can cause damage in the mouth, throat, stomach and intestines of the horse, which impairs the stamina and health of the horse.

Equine anthelmintics for the control of endoparasites are most usually administered in the form of a tablet, top dressing on grain, by stomach tube, paste or gel. Top dressings, tablets and tube administration are not effective modes of administration for controlling the first larval stage of endoparasites in the animal's mouth cavity.

The present invention relates to a novel composition containing butonate as the equine anthelmintic, which is particularly effective for the control of endoparasites in the animal's mouth. More particularly, the composition of the present invention is a gel formulation containing butonate characterized by: high effectiveness against endoparasites in the horse's mouth cavity; ease of administration; adherency, i.e., the horse is unable to eject or spit out the formulation; stability (including shelf life); and flowability over a wide temperature range. A further significant advantage is the ease of handling of the compositions of the present invention in the manufacture of final package forms, in that the compositions can be heated or warmed to become more fluid, making handling and filling easier without harm to the composition. On cooling, the composition returns to its gel form. The compositions of the present invention can be administered by syringe with a calibrated plunger by placing the syringe into the interdental space at the commissure of the horse's lip and thereby depositing the composition on the tongue and rear mouth cavity area. The composition cannot be spit out by the horse and consequently it very effectively treats the mouth cavity area where the first stage larvae are primarily located. As the composition is swallowed by the horse, it provides additional treatment of endoparasites in the throat and stomach areas. Common endoparasites of equine on which the composition of the present invention is useful include *Gastrophilus intestinalis* (common bot), *Gastrophilus hemorrhoidales* (nose bot), and *Gastrophilus nasalis* (throat or chin bot).

The anthelmintic or active ingredient in the compositions of the present invention has the common name butonate. It has been and is used to treat equine endoparasites via stomach tube administration. Butonate is dimethyl 2,2,2-trichloro-1-n-butyryloxyethylphosphonate and can be prepared as described in U.S. Pat. No. 2,911,435. The concentration of butonate in the compositions of the present invention can range from 10 to 95 percent, more usually 25 to 85 percent, by weight, of the total composition. Other anthelmintic or medicinal agents can be included in the composition, if desired, to accomplish a multi-purpose treatment; provided, however, that the added agent does not interfere with the characteristics of the composition given hereinabove.

Briefly stated, the gel composition of the present invention comprises, in addition to the anthelmintic, a primary thickening agent, an acid scavenger, an anti-oxidant and a secondary thickening agent. As the primary thickening agent, there is employed a polyhydric alcohol ester of a hydroxy-substituted fatty acid such as the glycerol ester of a hydroxy-substituted fatty acid. A preferred agent is glyceryl (tris)-12-hydroxyoleate and similar esters. As an acid scavenger, there is used an epoxidized linseed oil or epoxidized soybean oil. Suitable anti-oxidants include butylated hydroxytoluene, butylated hydroxyanisole, propyl gallate, or a tocopherol. As the secondary thickening agent, there is employed hydroxypropyl cellulose which may range from the relatively low molecular weight material (about 75,000) to the high molecular weight material (900,000). The presence of acid scavenger and anti-oxidant in the gel composition does not appear essential to the formation of the gel. However, for practical shelf-life of the gel composition, the acid scavenger, particularly, and an anti-oxidant are included in the preferred practice of the invention. A small amount of the acid scavenger and the anti-oxidant, generally about 0.5 to 5% of each, by weight of the total composition is used. The primary thickening agent and the secondary thickening agent, which are the basic components of the gel composition, can be adjusted over a wide range; however, in the preferred practice of the present invention, the primary and secondary thickening agents are used within the ratio of about 15:1 to about 3:1 or 8:1 to 5:1 parts by weight. In the case of hydroxy-propyl cellulose of high molecular weight, the amount used is small and thus toward or within the higher ratio, i.e. 15:1.

The following examples are provided to illustrate the practice of the present invention. All parts are part by weight.

EXAMPLE 1

To 91 parts butonate technical (95% purity), warmed to 50° C and while shearing with a propeller-type stirrer (6000 rpm), is added 2 parts Norfox 9-5 and 1 part Ionol. Then there is added 1 part Klucel L followed by 5 parts Geopon GO-13. Shearing is then continued for about 30 minutes to yield a gel which is allowed to cool to room temperature.

Norfox 9-5 is epoxidized linseed oil supplied by Norman, Fox and Company. Ionol is butylated hydroxytoluene supplied by Shell Oil Company. Klucel L is hydroxypropyl cellulose of a molecular weight of about 75,000 supplied by Hercules. Geopon GO-13 is glyceryl (tris)-12-hydroxyoleate supplied by NL Industries, Inc.

The chemical stability of the above composition was studied at 25° C and 37° C. Samples were stored in polyethylene syringes at the temperature indicated. As shown in Table I, the compositions contained 84.8% butonate and 83.2% butonate at 25° C and 37° C, respectively, after 6 months beginning with a theoretical of 86.5%.

TABLE I

| | Temp °C | Theory | Initial | 1 mo | 2 mo | 3 mo | 6 mo |
|---|---|---|---|---|---|---|---|
| Sample 1 | 25 | 86.5 | 87.0 | 84.2 | 85.7 | 83.5 | 84.8 |
| Sample 2 | 37 | 86.5 | 87.3 | 83.9 | 85.0 | 83.2 | 83.2 |

3.6 Grams of the composition of Example 1 was placed in the mouth, mostly on the rear tongue area, of a horse weighing about 1250 pounds, using a calibrated plastic syringe. The horse was not able to spit out or eject the composition and eventually swallowed all of the composition when it became more fluid from the warmth of the horse's mouth and shearing action of the horse's mouth.

The compositions of the present invention are administered into the horse's mouth at a dosage rate sufficient to supply an amount of active ingredient to be endoparacidally effective against first larval stage endoparasites. The dosage rate will vary according to the age and weight of the horse, primarily the weight. Generally, the dosage rate is between about 20 to 100 mg of active ingredient per kilogram of body weight, more usually, 40 to 75 mg/kilogram.

EXAMPLE 2

The procedure of Example 1 is repeated with the exception of using 0.5 parts of Klucel H (molecular weight about 900,000) in place of Klucel L to prepare a gel formulation of the present invention.

EXAMPLE 3

The procedure of Example 1 is repeated with the exception of using 5 parts of glyceryl (tris)-12-hydroxystearate in place of glyceryl (tris)-12-hydroxyoleate to prepare a gel formulation of the present invention.

What is claimed is:

1. An adhering gel composition for the control of equine endoparasites by application into the oral cavity which comprises in effective amounts
   (a) butonate,
   (b) a polyhydric alcohol ester of a hydroxy-substituted fatty acid as a primary thickening agent, and
   (c) hydroxypropyl cellulose as a secondary thickening agent.
2. A gel composition according to claim 1 wherein said primary thickening agent is a glycerol ester of a hydroxy-substituted fatty acid.
3. A gel composition according to claim 2 wherein said primary thickening agent is glyceryl (tris)-12-hydroxyoleate.
4. A gel composition according to claim 3 containing a small amount of an acid scavenger.
5. A gel composition according to claim 4 wherein the acid scavenger is epoxidized linseed oil or epoxidized soybean oil.
6. A gel composition according to claim 5 wherein said secondary thickening agent has a molecular weight of about 75,000.
7. A gel composition according to claim 5 wherein the ratio of primary thickening agent to secondary thickening agent is about 15:1 to about 3:1, parts by weight.
8. A gel composition according to claim 7 wherein the ratio is about 8:1 to 5:1.
9. A gel composition according to claim 8 wherein the hydroxypropyl cellulose has a molecular weight of about 75,000.

* * * * *